United States Patent [19]
Michaelis et al.

[11] Patent Number: 5,798,335
[45] Date of Patent: Aug. 25, 1998

[54] METHOD FOR THE TREATMENT OR PREVENTION OF ECZEMA/DERMATITIS

[75] Inventors: Jurgen Michaelis, Kariong; Timothy Elliot Trigg, Warawee, both of Australia

[73] Assignee: Peptide Technology Limited, Dee Why, Australia

[21] Appl. No.: 619,462

[22] PCT Filed: Sep. 26, 1994

[86] PCT No.: PCT/AU94/00574

§ 371 Date: May 7, 1996

§ 102(e) Date: May 7, 1996

[87] PCT Pub. No.: WO95/08338

PCT Pub. Date: Mar. 30, 1995

[30] Foreign Application Priority Data

Sep. 24, 1993 [AU] Australia ................. PM1449

[51] Int. Cl.$^6$ ............ A61K 38/00; A61K 38/08; C07K 7/00; C07K 7/04
[52] U.S. Cl. ............ 514/15; 514/8; 514/9; 514/16; 514/17; 514/18; 530/328; 530/329; 530/330
[58] Field of Search ............ 514/8, 15–18

[56] References Cited

U.S. PATENT DOCUMENTS 4,689,398  8/1987  Wu et al. .................. 530/327
5,063,206  11/1991  Bridge et al. .............. 514/16

FOREIGN PATENT DOCUMENTS

A 38953/93  10/1993  Australia .
92/14751    9/1992   WIPO .

OTHER PUBLICATIONS

SE 87/00125 (Wettenberg, L) 16 Jul. 1988, see abstract.

Johansson et al. Somatostatin immunoreactive cells in lesional psoriatic human skin during peptide treatment. Acta dermatol. Venerol., 74: 106–109, Jan. 1994.

Primary Examiner—Cecilia J. Tsang
Assistant Examiner—Michael Borin
Attorney, Agent, or Firm—Nixon & Vanderhye

[57] ABSTRACT

The present invention provides a method for the treatment or prevention of eczema/dermatitis. This method involves the administration of Peptide T or its derivatives or analogues. Preferred compounds used in the method include: 1) D-Ala-Ser-Thr-Thr-Thr-Asn-Tyr-Thr-NH$_2$; 2) Ala-Ser-thr-thr-Thr-Asn-Tyr-Thr, 3) D-Ala-Ser-Thr-Thr-Thr-Asn-Tyr-Thr, 4) D-Ala-Ala-Ser-Ser-Asn-Tyr-Met; 5) Thr-Asp-Asn-Tyr-Thr, 6) Thr-Thr-Ser-Tyr-Thr, 7) Thr-Thr-Asn-Tyr-Thr, 8) D-Thr-Thr-Tyr-D-Thr, 9) D-Ala-Ser-D-Thr-Thr-D-Thr-Asn-Tyr-D-Thr-NH$_2$; 10) D-Ser-Ser-D-Thr-Thr-D-Thr-Thr-Tyr-D-Thr-NH$_2$.

2 Claims, No Drawings

METHOD FOR THE TREATMENT OR PREVENTION OF ECZEMA/DERMATITIS

The present invention relates to the treatment or prevention of eczema/dermatitis.

The terms "eczema" and "dermatitis" are synonymous and will be used interchangeably throughout this specification.

BACKGROUND OF THE INVENTION

Eczema is a term that is widely, but often not consistently, used for a number of related skin complaints. Essentially, it is a reaction of the skin to a wide range of stimulants and irritants, some of which are known but many of which are unknown. The two classical criteria of the eruption in eczema are that it itches and that it causes vesication, or blistering, of the skin. Its first manifestation is often erythema. The next stage is usually the formation of vesicles or papules; these gradually break down and there is oozing from the affected area of the skin. If the condition persists, the skin may become thickened and to start scaling off.

Three common forms of eczema are nummular eczema, infective eczema and atopic eczema. Nummular eczema (or discoid eczema) consists of coin-shaped areas of eczema on the limbs which tend to itch intensely. Infective eczema is a form of eczema which can appear suddenly and spread rapidly in the area of a burn or cut. Atopic eczema is one of the most widespread and worrying forms of eczema; it often starts in infancy, at which stage its effects are particularly distressing, all the more so as the outlook for a cure is poor and the only effective local treatment is the application of hydrocortisone.

Eczema may be clearly contrasted with psoriasis. Psoriasis is a chronic skin disorder of unknown aetiology. It results from the overproduction of skin cells leading to thickening of the skin and scaling. Silvery plaques occur most frequently on the scalp, elbows, knees and lower back. In some instances the disease is so mild that persons never know they have it. At its worst, the disease can cover the entire body with redness and scaling.

Corticosteroid therapy, therefore, is to date the most successful remedial treatment for eczema. However, steroid chemotherapy is not without its drawbacks and hazards. Goodman and Gilman state, in "The Pharmacological Basis of Therapeutics", Seventh Edition, 1985:

"In clinical terms, the administration of corticosteroids for their anti-inflammatory effects is palliative therapy; the underlying cause of the disease remains; the inflammatory manifestations are merely suppressed. It is this suppression of inflammation and its consequence that has made the corticosteroids such valuable therapeutic agents—indeed, at times lifesaving. It is also this property that gives them a nearly unique potential for therapeutic disaster.

DESCRIPTION OF THE INVENTION

It has now been discovered that a group of non-steroidal compounds, namely peptide T and its derivatives and analogues, are useful in the prevention and treatment of Eczema.

Originally, many of the peptides useful in the invention were described as being effective in the prevention of infection and replication of HIV in vitro, see EP-A-0249390, EP-A-0249394 and WO-A-8809338, all of which are incorporated by reference to the maximum extent allowed by law, as are all other documents referred to in this specification. The compounds useful in the invention are also the subject of pending and as yet unpublished PCT patent application No. PCT/GB93/00649, filed 29 Mar. 1993. All compounds disclosed in these specifications are useful for the present invention. The original peptide has its basic point of origin in the octapeptide Ala-Ser-Thr-Thr-Thr-Asn-Tyr-Thr (SEQ ID No:1). It is called Peptide T because 50% of the amino acid residues are threonine.

Accordingly in a first aspect the present invention consists in a method of treating or preventing eczema in a subject comprising administering to the subject therapeutic amount of a linear or cyclic peptide of General Formula 1:

I-A-B-C-D-E-F-G-H-II     (General Formula 1) (SEQ ID No:2)

wherein A is Ala, Gly, Val, Ser, Thr or absent,

B is Ala, Gly, Val, Ser, Thr or absent,

C is Ser, Thr or absent,

D is Ser, Thr, Asn, Glu, Arg, Ile, Leu or absent,

E is Ser, Thr, Asp or absent,

F is Thr, Ser, Asn, Arg, Gln, Lys, Trp or absent,

G is Tyr, Phe, Trp, Leu, Met, Ile or absent,

H is Thr, Arg, Gly, Met, Met(O), Cys, Thr, Gly or absent,

I is Cys or absent,

II is Cys or absent, at least one of the amino acids optionally being substituted by a monomeric or polymeric carbohydrate or derivative thereof, such substitution being accomplished through hydroxyl and/or amino and/or amido groups of the amino acids, and wherein the peptide comprises at least four amino acid residues, or a pharmaceutically acceptable salt thereof.

Each of the amino acids referred to in General Formula 1 may be in the L- or D- stereoisomeric configuration and candidates for H may be esterified or amidated. The peptide comprises at least 4 amino acids.

Tetra-, penta-, hexa-, hepta-, octa- and non-peptides useful in the invention are all of the peptides chosen from the sequence:

I-A-B-C-D-E-F-G-H-II by deleting residues, for example, one at a time, from either the carboxyl or amino terminal, or from within the sequence.

It is appreciated that peptides having the core sequence of Thr-Thr-Asn-Tyr-Thr- (SEQ ID No:3) may have at both ends additional amino acid residues, some of which are represented by General Formula 2:

X-Ser-Thr-Thr-Thr-Asn-Tyr-Y (General Formula 2) (SEQ ID No:4)

wherein X is an amino acid terminal residue selected from Ala and D-Ala and Y is a carboxy terminal residue selected from Thr and Thr-amide.

A particular preferred peptide of the group of peptides has the aforementioned core sequence of -Thr-Thr-Asn-Tyr-Thr-. These peptides of the above General Formula 2, and in particular a variant Peptide T of the formula -Ser-Thr-Thr-Thr-Asn-Tyr-(SEQ ID No:5), were found to be very useful in inhibiting binding of the human immunodeficiency virus (HIV) to human cells by blocking receptor sites on the cell surfaces. The term Peptide T is used throughout the specification to reference, unless the context otherwise requires peptides of General Formula 2 which all include the core peptide sequence. It is therefore intended that Peptide T encompass all of the compounds of General Formula 2 where it is understood that all such compounds are variants of the normally understood octapeptide T, also referred to as prototype Peptide T, of the particular formula D-Ala-Ser-Thr-Thr-Thr-Asn-Tyr-Thr- amide.

The invention may be useful in both clinical (human) and veterinary medicine. The invention therefore has application in a method for treating or preventing Eczema, the method comprising administering to a human or other animal subject, for example on a repeated basis, a peptide of General Formula 1. The peptide will generally be administered in an effective, non-toxic amount or in such an amount that strikes an acceptable balance between efficacy and toxicity, having regard to the circumstances of the case.

Preferred peptides useful in the invention have as their active portion, an amino acid sequence of the formula:

-Thr-Thr-Asn-Tyr-Thr-

Most preferred peptides useful in the invention are the following:
1. D-Ala-Ser-Thr-Thr-Thr-Asn-Tyr-Thr-$NH_2$ (prototype Peptide T)
2. Ala-Ser-Thr-Thr-Thr-Asn-Tyr-Thr (SEQ ID No:6)
3. D-Ala-Ser-Thr-Thr-Thr-Asn-Tyr-Thr
4. D-Ala-Ala-Ser-Ser-Ser-Asn-Tyr-Met
5. Thr-Asp-Asn-Tyr-Thr (SEQ ID No:7)
6. Thr-Thr-Ser-Tyr-Thr (SEQ ID No:8)
7. Thr-Thr-Asn-Tyr-Thr
8. D-Thr-Thr-Tyr-D-Thr
9. D-Ala-Ser-D-Thr-Thr-D-Thr-Asn-Tyr-D-Thr-$NH_2$
10. D-Ser-Ser-D-Thr-Thr-D-Thr-Thr-Tyr-D-Thr-$NH_2$ Quite often it may be an advantage to have the amino terminal amino acid as a D-steroisomer, to protect the molecule from degradation from aminopeptidases; alternatively or additionally, the carboxy terminal amino acid may be an amino acid amide to protect the molecule from degradation from carboxypeptidases. In this connection, compounds 5, 6 and 7 listed above, include analogues with D-Thr as the amino terminal residue and/or an amide derivative at the carboxy terminal.

Furthermore, it should be understood that one more of the amino acids in the peptides may be substituted N-alkyl (eg ($C_1$-$C_4$) alkyl) amino acids instead of primary amino acids; examples include methyl and ethyl. The hydroxyl group side chains of one or more of the amino acids (Ser, Thr, Tyr) may be derivatised into an ether or ester group. Any (optionally substituted) alkyl ester or ether may be formed, such as ($C_1$-$C_4$) alkyl, aryl or aryl ($C_1$-$C_4$) alkyl esters, ethers, thioesters and thioethers, for example phenylester, benzylether or thiophenol ethylester. The presently preferred ethers are methyl, ethyl and propyl ethers and presently preferred esters are methyl, ethyl and propyl esters.

Furthermore, it should be understood that the C-terminal amide may be an alkyl amide with $C_1$-$C_6$ (linear, branched, or cyclic), the alkyl residue itself can be substituted with single or multiple groups such as hydroxy, fluoro, etc. Similarly, the N-terminal amino group may be acetylated with carboxylic acids of $C_1$-$C_6$ (linear, branched, or cyclic) which may be substituted with single or multiple groups such as hydroxy, fluoro, etc. Such derivations are to improve properties such as solubility, bioavailability and stability (physical, chemical, metabolic) rather than biological activity.

The hydroxyl side chains of the amino acids Ser, Thr and/or Tyr and the amido groups of the amino acids Asn and/or Gln may be substituted with different carbohydrates or derivatives of carbohydrates. Carbohydrate derivatives may be as discussed above.

Linear peptides useful in this invention may be prepared by any suitable process, such as conventional solid phase peptide synthetic techniques, see "Solid Phase Peptide Synthetic Techniques", 2nd ed. J. M. Stewart, J. D. Young, Pierce Chemical Company, 1984, ISBN: 0-935940-03-0. A frequently used solid phase method is the Merrifield technique. Another possibility is solution phase techniques. The preferred peptide, prototype Peptide T, is readily obtainable from Peptech (Europe), Hillesod, Denmark.

Cyclic peptides useful in the invention may be prepared by known techniques, such as, for example, described in Y. Hamada in *Tetrahedron Letters*, 26 5155 (1985). Cyclic peptides may be established in the form of a disulphide bridge between two Cys residues and/or by reacting the carboxy terminal amino acid residue with the amino terminal residue and/or by reacting the amino terminal residue with for example the g-carboxyl group of Glu, when Glu is at position D.

Carbohydrate derivatives may be prepared by methods known in the art. Glycosylated Peptide T is disclosed in Urge et al, *Biochem. Biophys. Res. Comms.* 184(2) 1125–1132 (1992), published 30 Apr. 1992, but the utility of the present invention is neither disclosed nor suggested.

Peptides useful in the invention may be administered as a composition in conjunction with a pharmaceutically acceptable carrier.

The peptides or peptide formulations may be used alone or in combination with any other pharmaceutically active compound, such as an anti-infective agent, for example an antibiotic and/or antiviral agent and/or antifungal agent, or another pharmaceutically active compound, such as an antineoplastic agent.

The peptides may be administered topically, orally, buccally, parenterally, rectally, vaginally, by intranasal inhalation spray, by intrapulmonary inhalation or in other ways. In particular, the peptides according to the invention may be formulated for topical application e.g. as sprays or creams. Further, the peptides according to the invention may be formulated for inhalation with spray or powder, for injection (for example subcutaneous, intramuscular, intravenous, intra-articular or intracisternal injection), for infusion or for oral administration and may be presented in unit dose form in ampoules or tablets or in multi-dose vials or other containers with an added preservative. The compositions may take such forms as suspensions, solutions, or emulsions or gels in oily or aqueous vehicles, and may contain formulatory agents such as suspending, stabilising and/or dispersing agents. Alternatively, the active ingredient may be in powder and/or lyophilised form for direct administration or for constitution with a suitable vehicle (eg sterile, pyrogen-free water, normal saline or 5% dextrose) before use. The pharmaceutical compositions containing peptide(s) may also contain other active ingredients such as antimicrobial agents, or preservatives.

The compositions may contain from 0.001–99% (w/v or, preferably, w/w) of the active material. Peptide T obtainable from Peptech (Europe) is usually formulated and packaged in a sterile manner in 5% dextrose solution in multi-dose vials. It will be appreciated that the peptide may be packaged in other carriers, such as saline. Preferably, the concentration of peptide in each dose is in the order of 8.5 mg/ml for subcutaneous injection in one ml doses.

The compositions are administered in therapeutically or prophylactic effective doses, i.e., 0.05–10000 mg of peptide per day, in particular 5–1000 mg per day. Very large doses may be used as the peptide according to the invention is non-toxic. However, normally this is not required. The dose administered daily of course depends on the degree of control required.

For administration by injection or infusion of the composition, the daily dosage, as employed for treatment of adults of approximately 70 kg of body weight, will often range from 0.2 mg to 20 mg of active material which may be administered in the form of 1 to 4 doses over each day, such dosage ranges depending upon the route of administration and the condition of the patient.

Compositions as described above may be prepared by mixing or otherwise bringing into association the ingredients.

The compounds useful in the invention may be used to treat or prevent any form of eczema, including but not being limited to nummular eczema, infective eczema and atopic eczema.

In order that the present invention may be more clearly understood preferred forms thereof will now be described with reference to the following examples.

EXAMPLE

The usefulness of the method of the present invention was assessed in experiments using dogs. The results of these experiments are set out below.

I. SUBJECT: DOG

| | |
|---|---|
| Assessment | Animal had three inflammatory lesions (severity 1*) on back. Lesions were approximately 2 cm in diameter and circular in shape. |
| Treatment | Dermal spray with Peptide T in water preparation. |
| Frequency of Treatment | Morning and afternoon. |
| Results | Lesions had disappeared after three days. |

II. SUBJECT: DESEXED BITCH

| | |
|---|---|
| Assessment | Severe inflammation (severity 2) on left side inner hind leg and along mid line. No scaliness or dryness, but obviously very itchy. Inflammation up mid line of belly extending from vulva ventrally for 6 inches and 2–3 inches on each side (severity 1). *No scaliness, but obvious centres of inflammation characterised by intense red spots. *Inflamed lower edges of upper lips and lower jaw (dermal surface). |
| Treatment and Results | 0.5 ml of peptide T (HCl) in glucose given subcutaneously on day 0, then 0.2 ml subcutaneously once per day for a further 6 days. Dermal spray on days 12 and 13. |

*Scale 0–3: Where 0 = no inflammation and 3 = very severe inflammation

RESULTS

| DAY | | TREATMENT | CHANGE IN ASSESSMENT |
|---|---|---|---|
| 0 | | 0.5 ml | |
| 1 | am | 22 | No change |
| | pm | 0.2 ml | No change |
| 2 | am | 22 | No change |
| | pm | 0.2 ml | No change |
| 3 | am | 22 | Slight reduction in extent of inflammation |
| | pm | 0.2 ml | No change |
| 4 | am | 22 | Slight improvement |
| | pm | 0.2 ml | No change |
| 5 | am | 22 | Much reduced inflammation |
| | pm | 0.2 ml | in leg, mid line and mouth. Improvement more noticeable at extreme end of leg (foot end of hip). |
| 6 | am | 22 | Inflammation general much better. Reduced to isolated spots |
| | pm | 0.2 ml | No change |
| 7 | am | 22 | No change |
| | pm | 0.2 ml | Spots disappeared |
| 8 | am | 22 | No change |
| | pm | 22 | No change |
| 9 | am | 22 | Inflammation returning |
| | pm | 22 | Inflammation worsening |
| 10 | am | 22 | As above |
| | pm | 22 | As above |
| 11 | am | 22 | Inflammation much worse. Past effected areas inflamed |
| | pm | 22 | As above |
| 12 | am | 22 | Very inflamed |
| | pm | Spray (dermal) | As above |
| 13 | am | Spray (dermal) | Inflammation reduced, more apparent on edges of legs |
| | pm | | |

END TRIAL

III. SUBJECT: DESEXED BITCH (Same animal as in II)

| | |
|---|---|
| Assessment | Inner left hand leg inflamed (Severity 1). Also two red spots in mid central line of belly, with light inflammation surrounding. |
| Treatment | Dermal spray with Peptide T (HCl) in water. |

RESULTS

| DAY | | TREATMENT | CHANGE IN ASSESSMENT |
|---|---|---|---|
| 1 | am | 22 | |
| | pm | spray | As above |
| 2 | am | spray | Slight improvement |
| | pm | spray | Spots of inflammation gone |
| 3 | am | 22 | No inflammation |
| | pm | 22 | No inflammation |
| 4 | am | 22 | No inflammation |
| | pm | 22 | No inflammation |
| 5 | am | spray | Midline inflammation |
| | pm | 22 | No change |
| 6 | am | spray | No change |

Following these initial trials a further trial was conducted casing 20 days. These animals all had a variety of skin conditions which had not responded well to other treatment regimes and to a large extent all animals were considered "incurable".

The trial was a double-blinded, placebo controlled trial in which the compound was compared with placebo treatment. The placebo is the same formulation as the treatment material, but without the active compound. The study was conducted as follows:

1. Assessment by a veterinarian.
2. Treatment Period A: 14 days.
3. Assessment by a veterinarian.

4. No treatment for seven days as a wash-out period.
5. Assessment by a veterinarian.
6. Treatment Period B: 14 days.
7. Assessment by a veterinarian.
8. No treatment for seven days.
9. Assessment by a veterinarian.

Neither the veterinarian, nor the owner knew which Treatment A or B contained the compound, until after the trial had been completed.

From this trial there was one case of improvement with the placebo, five cases of mild improvement in one parameter with Peptide T which was usually erythema and a significant improvement in two dogs treated with Peptide T. These two dogs were found to have atopic dermatitis. There was no change in ten of the dogs.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:1:

```
Ala  Ser  Thr  Thr  Thr  Asn  Tyr  Thr
1                   5
```

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Peptide
        ( B ) LOCATION: 1..10
        ( D ) OTHER INFORMATION: /product="OTHER"
        / note= "Xaa at position 1 is Cys or absent, Xaa at position 2 is Ala, Gly, Val, Ser, Thr or absent, Xaa at position 3 is Ala, Gly, Val, Ser, Thr or absent, Xaa at position 4 is Ser, Thr or absent, Xaa at position 5 is Ser, Thr, Asn, Glu, Arg, Ile, Leu or absent, Xaa at position 6 is Ser, Thr, Asp or absent, Xaa at position 7 is Thr, Ser, Asn, Arg, Gln, Lys, Trp or absent, Xaa at position 8 is Tyr, Phe, Trp, Leu, Met, Ile or absent, Xaa at position 9 is Thr, Arg, Gly, Met, Met(O), Cys, Thr, Gly or absent, and Xaa at position 10 is Cys or absent"

( x i ) SEQUENCE DESCRIPTION: SEQ ID NO:2:

```
Xaa  Xaa  Xaa  Xaa  Xaa  Xaa  Xaa  Xaa  Xaa  Xaa
1                   5                        10
```

( 2 ) INFORMATION FOR SEQ ID NO:3:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:3:

Thr Thr Asn Tyr Thr
1               5

( 2 ) INFORMATION FOR SEQ ID NO:4:

( i ) SEQUENCE CHARACTERISTICS:
    ( A ) LENGTH: 8 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( A ) NAME/KEY: Peptide
    ( B ) LOCATION: 1..8
    ( D ) OTHER INFORMATION: /product="OTHER"
      / note= "Xaa at position 1 is Ala or D-Ala and Xaa at
      position 8 is Met, Thr or Thr-amide"

( x i ) SEQUENCE DESCRIPTION: SEQ ID NO:4:

Xaa Ser Thr Thr Thr Asn Tyr Xaa
1               5

( 2 ) INFORMATION FOR SEQ ID NO:5:

( i ) SEQUENCE CHARACTERISTICS:
    ( A ) LENGTH: 6 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:5:

Ser Thr Thr Thr Asn Tyr
1               5

( 2 ) INFORMATION FOR SEQ ID NO:6:

( i ) SEQUENCE CHARACTERISTICS:
    ( A ) LENGTH: 8 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:6:

Ala Ser Thr Thr Thr Asn Tyr Thr
1               5

( 2 ) INFORMATION FOR SEQ ID NO:7:

( i ) SEQUENCE CHARACTERISTICS:
    ( A ) LENGTH: 5 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:7:

Thr Asp Asn Tyr Thr
1               5

( 2 ) INFORMATION FOR SEQ ID NO:8:

(  i  ) SEQUENCE CHARACTERISTICS:
   ( A ) LENGTH: 5 amino acids
   ( B ) TYPE: amino acid
   ( C ) STRANDEDNESS:
   ( D ) TOPOLOGY: linear (  i i  ) MOLECULE TYPE: peptide (  x i  ) SEQUENCE DESCRIPTION: SEQ ID NO:8:

Thr Thr Ser Tyr Thr
1           5

We claim:

1. A method of treating eczema and/or dermatitis in a subject, comprising administering to the subject a therapeutic amount of the peptide D-Ala-Ser-Thr-Thr-Thr-Thr-Asn-Tyr-Thr-NH$_2$.

2. A method as claimed in claim 1, wherein the peptide is administered as a composition in conjunction with a pharmaceutically acceptable carrier.

* * * * *